United States Patent [19]

Gleason

[11] 4,020,057

[45] Apr. 26, 1977

[54] 7β-ACYLOXY CEPHALOSPORINS

[75] Inventor: John G. Gleason, Delran, N.J.

[73] Assignee: SmithKline Corporation, Philadelphia, Pa.

[22] Filed: June 18, 1975

[21] Appl. No.: 588,096

[52] U.S. Cl. .................. 260/243 C; 260/306.7 C; 424/246

[51] Int. Cl.$^2$ ..................................... C07D 501/00

[58] Field of Search ................ 260/243 C, 306.7 C

[56] References Cited

FOREIGN PATENTS OR APPLICATIONS 9,049,982  9/1972  Japan

OTHER PUBLICATIONS

Sheehan et. al., "J. Org. Chem." 39:1444 (1974).

*Primary Examiner*—Nicholas S. Rizzo
*Assistant Examiner*—David E. Wheeler
*Attorney, Agent, or Firm*—Janice E. Williams; William H. Edgerton; Alan D. Lourie

[57] ABSTRACT

The compounds of this invention are cephalosporins having a 7β-acyloxy group and 7β-hydroxy intermediates for the preparation thereof. The compounds have antibacterial activity.

3 Claims, No Drawings

7β-ACYLOXY CEPHALOSPORINS

This invention relates to a new series of cephalosporin compounds which have antibacterial activity and to intermediates for the preparation thereof. In particular, the biologically active cephalosporin compounds of this invention are characterized by having an acyloxy group at the 7β-position of the cephem nucleus. Also, this invention extends to methods and compositions for treating certain bacterial infections using these new compounds.

The compounds of this invention are represented by the following structural formula:

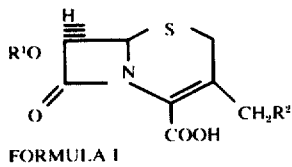

FORMULA I in which:

$R^1$ is an acyl group selected from the group consisting of:

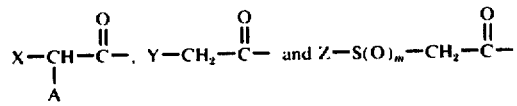

where:

X is thienyl; dihydrophenyl; phenyl; phenyl monosubstituted with hydroxy, hydroxymethyl, formamido, ureido, carboxymethylamino; 3-fluoro-4-hydroxyphenyl or 3,4-dihydroxyphenyl;

A is $NH_2$, OH, COOH or $SO_3H$, or formyloxy when X is phenyl;

Y is thienyl, tetrazolyl, phenoxy, cyano, sydnone or aminomethylphenyl;

Z is methyl, trifluoromethyl, trifluoroethyl, cyanomethyl or pyridyl;

$m$ is zero to two; and $R^2$ is acetoxy or SHet where Het is a five or six membered heterocyclic ring containing carbon and one to four atoms selected from the group consisting of N, O and S, each such ring being unsubstituted or substituted with from one to two groups selected from lower alkyl, alkoxyalkyl and trifluoromethyl, each alkyl or alkoxy group having from one to four carbon atoms, or a non-toxic pharmaceutically acceptable salt thereof.

It will be recognized that the 4-carboxylic acid group of the compounds of Formula I may be readily esterified by methods well known to the art. These esters include, for example, simple alkyl and aryl esters as well as esters which are easily cleaved within the body to the parent acid such as indanyl, pivaloyloxymethyl, acetoxymethyl, propionyloxymethyl, glycyloxymethyl, phenylglycyloxymethyl and thienylglycyloxymethyl esters and other. Of course, when A is COOH, this group may be similarly esterified. All such esters are included within the scope of this invention.

Preferred compounds of this invention are represented by Formula I where $R^2$ is acetoxy or SHet and Het is unsubstituted or methyl substituted 1,2,3-triazolyl, 1,2,4-triazolyl, 1,2,3,4-tetrazolyl, oxazolyl, thiazolyl, 1,3,4-oxadiazolyl, 1,3,4-thiadiazolyl or 1,2,4-thiadiazolyl.

Advantageous compounds of this invention are represented by Formula I where X is phenyl, A is $NH_2$ or OH, Y is thienyl or phenoxy, Z is trifluoromethyl, $m$ is zero and $R^2$ is acetoxy.

Examples of the most preferred 7β-acyloxy substituents ($R^1O$—) of the compounds of Formula I are listed below:

α-hydroxyphenylacetoxy
α-aminophenylacetoxy
α-amino-4-hydroxyphenylacetoxy
trifluoromethylmercaptoacetoxy
methylmercaptoacetoxy
2,2,2-trifluoroethylsulfinylacetoxy
thienylacetoxy
tetrazolylacetoxy
cyanoacetoxy
phenoxyacetoxy
α-carboxythienylacetoxy
α-carboxyphenylacetoxy
α-sulfophenylacetoxy
methylsulfonylacetoxy
cyanomethylmercaptoacetoxy
α-amino-4-carboxymethylaminophenylacetoxy
α-amino-3-fluoro-4-hydroxyphenylacetoxy
3-sydnoneacetoxy
4-pyridylthioacetoxy
2-aminomethylphenylacetoxy.

Particularly preferred are the compounds 7β-(D-α-aminophenylacetoxy)cephalosporanic acid, 7β-phenoxyacetoxycephalosporanic acid, 7β-trifluoromethylmercaptoacetoxycephalosporanic acid and 7β-(D-α-hydroxyphenylacetoxy)cephalosporanic acid.

Cephalosporins containing a 7α-hydroxy group with a methyl or acetoxymethyl substituent at the 3-position have been described by Sheehan et al. [J. Org. Chem. 39:1444 (1974)]. Japanese Pat. No. 9049982 discloses 7-acyloxy(desacetoxycephalosporanic and -cephalosporanic)acid esters. Specifically described is the compound 7α-phenoxyacetoxy-3-desacetoxycephalosporanic acid methyl ester. No examples of the 7β-hydroxy and 7β-acyloxy cephalosporins of this invention, however, are believed to be known to the art.

The compounds of Formula I are prepared by esterification of an appropriate 7β-hydroxy cephalosporin nucleus of Formula II:

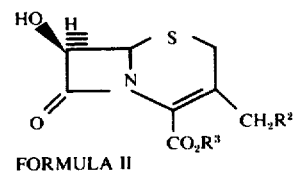

FORMULA II in which:

$R^2$ is acetoxy or SHet where Het is a five or six membered heterocyclic ring containing carbon and one to four atoms selected from the group consisting of N, O and S, each such ring being unsubstituted or substituted with from one to two groups selected from lower alkyl, alkoxyalkyl and trifluoromethyl, each alkyl or alkoxy group having from one to four carbon atoms; and $R^3$ is hydrogen or an easily removable ester protecting group, by well known esterification methods, for example by reaction of a compound of Formula II with an appropriate acid (R$^1$OH) or other esterifying agent, preferably an acid chloride (R$^1$Cl), followed by removal of the protective groups when present.

The carboxylic acid group of the esterifying agent may be activated by any of the standard methods such as conversion to the mixed anhydride, acid imidazolide or activated ester. In addition, a reagent such as dicyclohexylcarbodiimide can be used provided that the carboxyl group on the cephem nucleus is protected with an easily removable ester protecting group.

The term "easily removable ester protecting group" is one which has acquired a definite meaning within the cephalosporin and peptide art. Many such groups are known which are used to protect the carboxyl group during subsequent chemical reactions and are later removed by standard methods to give the free carboxylic acid. Known ester protecting groups include 2,2,2-trichloroethyl, $C_4$–$C_6$-tertiary alkyl, $C_5$–$C_7$-tertiary alkenyl, $C_5$–$C_7$-tertiary alkynyl, $C_1$–$C_6$-alkanoylmethyl, N-phthalimidomethyl, benzoylmethyl, halobenzoylmethyl, methylbenzoylmethyl, methanesulfonylbenzoylmethyl, phenylbenzoylmethyl, benzyl, nitrobenzyl, methoxybenzyl, benzyloxymethyl, nitrophenyl, methoxyphenyl, benzhydryl, trityl, trimethylsilyl, triethylsilyl and the like. The choice of an ester protecting group is well within the ability of one skilled in the art. Factors which are considered include the subsequent reaction conditions the group must withstand and the conditions desired for removing the protecting group. Because the novelty of this invention lies within the new bicyclic nucleus, the choice of a protecting group is not critical to the invention.

When A is NH$_2$, the α-amino group of the esterifying agent is, preferably, protected prior to esterification with an easily removable amine protecting group. The term "easily removable amine protecting group" is well known in the art and includes many groups commonly used in the synthesis of cephalosporins and peptides. These include trityl, t-butoxycarbonyl, trichloroethoxycarbonyl, benzyloxycarbonyl, the methyl acetoacetate adduct and the like. Divalent amine protecting groups include phthaloyl, imines and similar groups. The choice of the protecting group depends on various factors such as the subsequent chemical reaction conditions the group must withstand and the conditions desired for removing the protecting group and are within the ordinary ability of one skilled in the art. As with the ester protecting groups, the choice of the amine protecting group is not critical to this invention.

The compounds represented by Formula II above are also considered as objects of this invention.

The compounds of Formula I where R$^2$ is SHet are also prepared by displacement of a 7β-acyloxy cephalosporanic acid with a mercaptoheterocycle in an aqueous, slightly basic medium.

The protective groups can be removed according to methods well known to the art, such as with trifluoroacetic acid when t-butyl or t-butoxycarbonyl protective groups are used. The resulting salt is converted to the zwitterionic product or to the free acid by means of a basic ion exchange resin such as polystyrene-amine ion exchange resin (Amberlite IR-45) or else by basification of an aqueous solution of the salt.

The esterifying agents used as starting materials are either known or prepared by known methods.

The 7β-hydroxy cephalosporin starting materials of Formula II are prepared by reduction of the corresponding 7-oxo cephalosporins of Formula III:

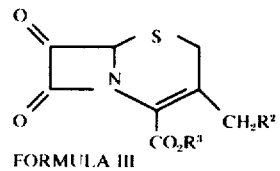

FORMULA III where R$^2$ is defined as above and R$^3$ is an easily removable ester protecting group with, for example, a metal hydride reducing agent such as sodium borohydride according to standard procedures.

The 7-oxo cephalosporins of Formula III are prepared by treatment of an ester of the corresponding 7-amino cephalosporin with 3,5-di-t-butyl-1,2-dioxobenzene, prepared by oxidation of 3,5-di-t-butylcatechol with for example silver oxide, followed by acid hydrolysis of the product thus formed.

The compounds of this invention are capable of forming salts with, for example, the alkali metals such as sodium or potassium, the alkaline earth metals such as calcium or with the ammonium cation. When A is NH$_2$, the compounds can exist as the zwitterion or as an acid or base salt. These salts are prepared by standard methods using a wide variety of non-toxic pharmaceutically acceptable acids and bases known in the art and are also considered as objects of this invention.

It will be recognized that due to the asymmetric α-carbon atom in the 7β-acyloxy group of Formula I when R$^1$ is

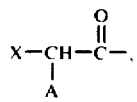

optical isomers will exist. Racemic or resolved products are obtained depending upon whether a racemic or resolved side chain acid is used as an esterifying agent. The resolved side chain acids are readily obtained from the racemic compounds by resolution according to well known methods, including fractional crystallization of a salt formed with an optically active acid or base. All of the isomers, including separated isomers and mixtures thereof, are included within the scope of this invention.

The compounds of Formula I above are effective antibacterial agents and exhibit activity against, for example Staph.Aureus, Klebsiella and Enterobacter bacteria.

Pharmaceutical compositions having antibacterial activity which comprise a pharmaceutical carrier containing an active but non-toxic quantity of a compound of Formula I as well as methods of combatting bacterial infections by administering such a composition to an infected host in a nontoxic amount sufficient to combat such infections are also objects of this invention. The administration may be orally or by parenteral injection such as subcutaneously, intramuscularly or intravenously. The injection of suitably prepared sterile solutions or suspensions containing an effective, nontoxic amount of the new cephalosporin compound is the preferred route of administration.

The compounds of Formula I are formulated and administered in the same manner as other cephalosporins. The dosage regimen comprises administration, preferably by injection, of an active but nontoxic quantity of a compound of Formula I. The precise dosages are dependent upon the age and weight of the subject and on the infection being treated and can be determined by those skilled in the art based on the data disclosed herein compared with that available to the art attained with known cephalosporins.

The following examples illustrate the invention, but are not to be construed as limiting the scope thereof. Temperatures are in degrees Centigrade unless otherwise stated.

EXAMPLE 1

7β-Hydroxycephalosporanic acid

To a solution of 5 g. (22.5 mmol.) of 3,5-di-t-butylcatechol in 75 ml. of ether at 0° was added 25 g. of silver oxide. The reaction mixture was stirred at 0° for 30 minutes then at ambient temperature for an additional 30 minutes. The mixture was filtered and the filtrate was evaporated to dryness. Benzene was added to the residue and the resulting precipitate was collected by filtration and air dried to give 3,5-di-t-butyl-1,2-dioxobenzene, m.p. 110°–112°.

A solution of 3.28 g. (10 mmol.) of 7-aminocephalosporanic acid t-butyl ester and 2.20 g. (10 mmol.) of 3,5-di-t-butyl-1,2-dioxobenzene in 50 ml. of tetrahydrofuran containing 5 g. of 5A molecular sieves was maintained at 4° for 12 hours. The mixture was filtered, 3 g. of oxalic acid and 10 ml. of water were added to the filtrate and the solution was allowed to stand at 4° for 12 hours. The tetrahydrofuran was evaporated and the aqueous residue was partitioned between 50 ml. of benzene and 50 ml. of water. The insoluble material was removed by filtration, the layers were separated and the organic phase was diluted with hexane and extracted with water. Sodium chloride solution was added to the combined aqueous phases, and they were extracted with ether. The ether extract was dried and evaporated to near dryness. Addition of benzene and hexane containing water induced crystallization of 7-oxocephalosporanic acid t-butyl ester hydrate.

A solution of 1.38 g. (4 mmol.) of 7-oxocephalosporanic acid t-butyl ester hydrate in 50 ml. of isopropanol and 3 ml. of water was cooled to 0° (ice bath) and 0.150 g. (4 mmol.) of sodium borohydride was added with stirring. The reaction mixture was stirred for 5 minutes then decomposed by addition of acetic acid. The mixture was extracted with ethyl acetate and the organic phase was washed with water, dried (MgSO$_4$) and evaporated to dryness to give a residue which was recrystallized from ethyl acetate-hexane to give 7β-hydroxycephalosporanic acid t-butyl ester.

$C_{14}H_{19}NO_6S \cdot 0.25\ H_2O$

Calculated: 50.36% C; 5.89% H; 4.20% N. Found: 50.64% C; 5.95% H; 4.02% N.

7β-Hydroxycephalosporanic acid t-butyl ester (1.0 g.) was stirred in 10 ml. of trifluoroacetic acid containing 1% anisole at 25° for 2 hours. The reaction mixture was evaporated to dryness, the residue was triturated with etherhexane and the precipitated product was collected and recrystallized from tetrahydrofuran-hexane to give the title compound.

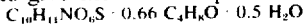

Calculated: 46.03% C; 5.29% H; 4.26% N. Found: 46.38% C; 5.12% H; 3.90% N.

EXAMPLE 2

7β-(D-α-aminophenylacetoxy)cephalosporanic acid

To a solution of 0.126 g. (0.5 mmol.) of D-N-t-butoxycarbonylphenylglycine in 10 ml. of tetrahydrofuran at −15° under a nitrogen atmosphere was added 0.075 ml. (0.5 mmol.) of triethylamine followed by 0.039 ml. (0.5 mmol.) of ethyl chloroformate. The mixture was stirred for 15 minutes then a solution of 0.165 g. (0.5 mmol.) of 7β-hydroxycephalosporanic acid t-butyl ester in 25 ml. of tetrahydrofuran was slowly added and the resulting mixture was stirred at 0° for 1 hour, then at ambient temperature for 12 hours. Water was added to the reaction mixture and it was extracted repeatedly with ether. The combined extracts were washed with saturated sodium chloride solution, dried and evaporated to dryness to give a residue which was chromatographed on silica with benzene-ethyl acetate as eluant to give 7β-(D-α-N-t-butoxycarbonylaminophenylacetoxy)cephalosporanic acid t-butyl ester.

7β-(D-α-N-t-Butoxycarbonylaminophenylacetoxy)-cephalosporanic acid t-butyl ester (0.2 g.) was stirred with 20% trifluoroacetic acid in methylene chloride containing anisole at 25° for 3 hours. The solution was evaporated to dryness and the residue was washed with hexane. Ether was added to the residue to give the title compound.

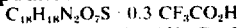

Calculated: 46.16% C; 3.68% H; 5.38% N. Found: 50.81% C; 4.30% H; 6.35% N.

EXAMPLE 3

7β-Trifluoromethylmercaptoacetoxycephalosporanic acid

A solution of 0.40 g. (2.5 mmol.) of trifluoromethylmercaptoacetic acid and 0.35 g. (2.75 mmol.) of oxalyl chloride in 3 ml. of benzene was cooled to 0° and 0.20 g. of pyridine in 1 ml. of benzene was added under an argon atmosphere. The reaction mixture was stirred for 15 minutes then filtered. The filtrate was added dropwise to a stirred solution of 0.66 g. (2.0 mmol.) of 7β-hydroxycephalosporanic acid t-butyl ester in 80 ml. of ether containing 0.15 ml. of pyridine at 0°. After addition, the mixture was stirred at 25° for 0.5 hour then ice water was added and the layers were separated. The aqueous phase was thoroughly extracted with ether, and the combined organic phases were washed with saturated sodium chloride solution, dried and evaporated to dryness to give a residue which was chromatographed on silica with benzene-ethyl acetate as eluent to give 7β-trifluoromethylmercaptoacetoxycephalosporanic acid t-butyl ester.

7β-Trifluoromethylmercaptoacetoxycephalosporanic acid t-butyl ester (0.4 g.) was stirred in 10 ml. of trifluoroacetic acid of 25° for 3 hours. The solution was evaporated to dryness to give the title compound.

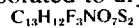

Calculated: 37.59% C; 3.06% H; 3.37% N. Found: 37.67% C; 3.06% H; 3.00% N.

EXAMPLE 4

7β-Phenoxyacetoxycephalosporanic acid

To a solution of 0.448 g. (1.35 mmol.) of 7β-hydroxycephalosporanic acid t-butyl ester and 0.1 ml. of pyridine in 60 ml. of anhydrous ether at 0° was added 0.24 g. (1.4 mmol.) of phenoxyacetylchloride. The reaction mixture was stirred for 1 hour in the cold then for 30 minutes at ambient temperature. Cold water was added to the mixture, the layers were separated and the aqueous phase was extracted repeatedly with ether. The combined ether layers were washed with saturated sodium chloride solution, dried ($Na_2SO_4$) and evaporated to dryness. The residue was chromatographed on silica with benzene-ethyl acetate as eluant to give 7β-phenoxyacetoxycephalosporanic acid t-butyl ester.

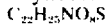

Calculated: 57.01% C; 5.44% H; 3.02% N. Found: 57.48% C; 5.54% H; 2.60% N.

7β-Phenoxyacetoxycephalosporanic acid t-butyl ester was treated with trifluoroacetic acid as previously described to give the title compound.

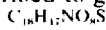

Calculated: 53.07% C; 4.21% H; 3.44% N. Found: 53.12% C; 4.30% H; 3.24% N.

EXAMPLE 5

7β-(D-α-Hydroxyphenylacetoxy)cephalosporanic acid

To a solution of 0.659 g. (2.0 mmol.) of 7β-hydroxycephalosporanic acid t-butyl ester in 60 ml. of methylene chloride containing 0.16 ml. of pyridine at 0° under a nitrogen atmosphere was added 0.600 g. (2.2 mmol.) of D-O-dichloroacetylmandeloyl chloride in 10 ml. of methylene chloride. The reaction mixture was stirred for 30 minutes in the cold, then warmed to ambient temperature. The aqueous phase was thoroughly extracted with methylene chloride. The organic layers were combined, washed with saturated sodium chloride, dried ($Na_2SO_4$) and evaporated to dryness to give a residue which was chromatographed on silica with benzeneethyl acetate as eluant to give 7β-(D-α-dichloroacetoxyphenylacetoxy)cephalosporanic acid t-butyl ester.

7β-(D-α-Dichloroacetoxyphenylacetoxy)cephalosporanic acid t-butyl ester (0.60 g.) was stirred with 50 ml. of 20% trifluoroacetic acid in methylene chloride containing anisole at 25° for 2 hours. The solution was evaporated to dryness and the residue was washed with hexane and chromatographed on silica with 1% acetic acid in benzeneethyl acetate as eluant to give 7β-(D-α-dichloroacetoxyphenylacetoxy)cephalosporanic acid.

7β-(D-α-Dichloroacetoxyphenylacetoxy)cephalosporanic acid (0.330 g.) was dissolved in acetone and a solution of 3:1 0.1M $Na_2HPO_4$:0.1M $NaH_2PO_4$ buffer was added dropwise until pH 7.2. The solution was allowed to stand for 20 minutes then it was cooled and acidified with dilute phosphoric acid until pH 1.5. The acidic solution was extracted with ether and the extract was washed with saturated sodium chloride solution, dried ($MgSO_4$) and evaporated to dryness. The residue was crystallized from ethyl acetate-hexane to give the title compound.

EXAMPLE 6

When 7β-hydroxycephalosporanic acid t-butyl ester is esterified (acylated) with other esterifying (acylating) agents known to the art, particularly with an acid or activated form of an acid listed below, suitably protected as necessary:

α-amino-4-hydroxyphenylacetic acid
methylmercaptoacetic acid
2,2,2-trifluoroethylsulfinylacetic acid
2-thienylacetic acid
1-tetrazolylacetic acid
cyanoacetic acid
α-carboxy-2-thienylacetic acid
α-carboxyphenylacetic acid
α-sulfophenylacetic acid
methylsulfonylacetic acid
cyanomethylmercaptoacetic acid
α-amino-4-carboxymethylaminophenylacetic acid
α-amino-3-fluoro-4-hydroxyphenylacetic acid
3-syndnoneactic acid
4-pyridylthioacetic acid
2-aminomethylphenylacetic acid according to the procedures described in Examples 2, 3, 4 or 5 followed by removal of the protective groups when necessary as described therein, the corresponding 7β-acyloxycephalosporanic acids are prepared.

EXAMPLE 7

When the t-butyl ester of a 7-amino-3-heterocyclic-thiomethyl cephalosporin listed below:

7-amino-3-(1-methyltetrazol-5-ylthiomethyl)-3-cephem-4-carboxylic acid
7-amino-3-(4-methyl-1,2,4-triazol-3-ylthiomethyl)-3-cephem-4-carboxylic acid
7-amino-3-(1,3,4-thiadiazol-2-ylthiomethyl)-3-cephem-4-carboxylic acid.
7-amino-3-(5-methyl-1,3,4-thiadiazol-2-ylthiomethyl)-3-cephem-4-carboxylic acid
7-amino-3-(5-ethyl-1,3,4-thiadiazol-2-ylthiomethyl)-3-cephem-4-carboxylic acid
7-amino-3-(5-trifluoromethyl-1,3,4-thiadiazol-2-ylthiomethyl)-3-cephem-4-carboxylic acid
7-amino-3-(5-n-butyl-1,3,4-thiadiazol-2-ylthiomethyl)-3-cephem-4-carboxylic acid
7-amino-3-(1,2,4-thiadiazol-5-ylthiomethyl)-3-cephem-4-carboxylic acid
7-amino-3-(3-methyl-1,2,4-thiadiazol-5-ylthiomethyl)-3-cephem-4-carboxylic acid
7-amino-3-(3-ethyl-1,2,4-thiadiazol-5-ylthiomethyl)-3-cephem-4-carboxylic acid
7-amino-3-(thiazol-5-ylthiomethyl)-3-cephem-4-carboxylic acid
7-amino-3-(2-methylthiazol-5-ylthiomethyl)-3-cephem-4-carboxylic acid
7-amino-3-(4-methylthiazol-5-ylthiomethyl)-3-cephem-4-carboxylic acid
7-amino-3-(2,4-dimethylthiazol-5-ylthiomethyl)-3-cephem-4-carboxylic acid
7-amino-3-(2-ethylthiazol-5-ylthiomethyl)-3-cephem-4-carboxylic acid
7-amino-3-(4-ethylthiazol-5-ylthiomethyl)-3-cephem-4-carboxylic acid
7-amino-3-(2,4-diethylthiazol-5-ylthiomethyl)-3-cephem-4-carboxylic acid
7-amino-3-(1,3,4-oxadiazol-2-ylthiomethyl)-3-cephem-4-carboxylic acid
7-amino-3-(5-methyl-1,3,4-oxadiazol-2-ylthiomethyl)-3-cephem-4-carboxylic acid
7-amino-3-(oxazol-5-ylthiomethyl)-3-cephem-4-carboxylic acid
7-amino-3-(2-methyloxazol-5-ylthiomethyl)-3-cephem-4-carboxylic acid
7-amino-3-(4-methyloxazol-5-ylthiomethyl)-3-cephem-4-carboxylic acid
7-amino-3-(2,4-dimethyloxazol-5-ylthiomethyl)-3-cephem-4-carboxylic acid
7-amino-3-(2-ethyloxazol-5ylthiomethyl)-3-cepham-4-carboxylic acid 7-amino-3-(4-ethyloxazol-5-ylthiomethyl)-3-cephem-4-carboxylic acid
7-amino-3-(2,4-diethyloxazol-5-ylthiomethyl)-3-cephem-4-carboxylic acid
7-amino-3-(tetrazol-5-ylthiomethyl)-3-cephem-4-carboxylic acid
7-amino-3-(1-ethyltetrazol-5-ylthiomethyl)-3-cephem-4-carboxylic acid
7-amino-3-(1,2,4-triazol-3-ylthiomethyl)-3-cephem-4-carboxylic acid
7-amino-3-(5-methyl-1,2,4-triazol-3-ylthiomethyl)-3-cephem-4-carboxylic acid
7-amino-3-(1-methyl-1,2,4-triazol-5-ylthiomethyl)-3-cephem-4-carboxylic acid
7-amino-3-(1,5-dimethyl-1,2,4-triazol-3-ylthiomethyl)-3-cephem-4-carboxylic acid
7-amino-3-(4,5-dimethyl-1,2,4-triazol-3-ylthiomethyl)-3-cephem-4-carboxylic acid
7-amino-3-(4-ethyl-1,2,4-triazol-3-ylthiomethyl)-3-cephem-4-carboxylic acid
7-amino-3-(5-ethyl-1,2,4-triazol-3-ylthiomethyl)-3-cephem-4-carboxylic acid
7-amino-3-(1-ethyl-1,2,4-triazol-5-ylthiomethyl)-3-cephem-4-carboxylic acid
7-amino-3-(4,5-diethyl-1,2,4-triazol-3-ylthiomethyl)-3-cephem-4-carboxylic acid
7-amino-3-(1,3-diethyl-1,2,4-triazol-5-ylthiomethyl)-3-cephem-4-carboxylic acid
7-amino-3-(4-methoxymethyl-1,2,4-triazol-3-ylthiomethyl)-3-cephem-4-carboxylic acid
7-amino-3-(4-methyl-5-trifluoromethyl-1,2,4-triazol-3-ylthiomethyl)-3-cephem-4-carboxylic acid
7-amino-3-(1,2,3-triazol-4-ylthiomethyl)-3-cephem-4-carboxylic acid
7-amino-3-(3-methyl-1,2,3-triazol-4-ylthiomethyl)-3-cephem-4-carboxylic acid
7-amino-3-(5-methyl-1,2,3-triazol-4-ylthiomethyl)-3-cephem-4-carboxylic acid
7-amino-3-(3,5-dimethyl-1,2,3-triazol-4-ylthiomethyl)-3-cephem-4-carboxylic acid
7-amino-3-(3-ethyl-1,2,3-triazol-4-ylthiomethyl)-3-cephem-4-carboxylic acid
7-amino-3-(5-ethyl-1,2,3-triazol-4-ylthiomethyl)-3-cephem-4-carboxylic acid
7-amino-3-(3,5-diethyl-1,2,3-triazol-4-ylthiomethyl)-3-cephem-4-carboxylic acid
7-amino-3-(3-methoxymethyl-1,2,3-triazol-4-ylthiomethyl)-3-cephem-4-carboxylic acid
7-amino-3-(4-pyridylthiomethyl)-3-cephem-4-carboxylic acid
7-amino-3-(3-pyridylthiomethyl)-3-cephem-4-carboxylic acid
7-amino-3-(4-pyrimidylthiomethyl)-3-cephem-4-carboxylic acid
7-amino-3-(2-pyrazinylthiomethyl)-3-cephem-4-carboxylic acid is substituted in the procedure of Example 1 for 7-aminocephalosporanic acid t-butyl ester, the resulting 7-oxo-3-heterocyclicthiomethyl-3-cephem-4-carboxylic acid t-butyl ester is reduced with sodium borohydride as described therein and the reduced product is treated with trifluoroacetic acid as described above to remove the t-butyl ester, the following 7β-hydroxy-3-heterocyclicthiomethyl-3-cephem-4-carboxylic acids are obtained:

7β-hydroxy-3-(1-methyltetrazol-5-ylthiomethyl)-3-cephem-4-carboxylic acid
7β-hydroxy-3-(4-methyl-1,2,4-triazol-3-ylthiomethyl)-3-cephem-4-carboxylic acid
7β-hydroxy-3-(1,3,4-thiadiazol-2-ylthiomethyl)-3-cephem-4-carboxylic acid
7β-hydroxy-3-(5-methyl-1,3,4-thiadiazol-2-ylthiomethyl)-3-cephem-4-carboxylic acid
7β-hydroxy-3-(5-ethyl-1,3,4-thiadiazol-2-ylthiomethyl)-3-cephem-4-carboxylic acid
7β-hydroxy-3-(5-trifluoromethyl-1,3,4-thiadiazol-2-ylthiomethyl)-3-cephem-4-carboxylic acid
7β-hydroxy-3-(5-n-butyl-1,3,4-thiadiazol-2-ylthiomethyl)-3-cephem-4-carboxylic acid
7β-hydroxy-3-(1,2,4-thiadiazol-5-ylthiomethyl)-3-cephem-4-carboxylic acid
7β-hydroxy-3-(3-methyl-1,2,4-thiadiazol-5-ylthiomethyl)-3-cephem-4-carboxylic acid
7β-hydroxy-3-(3-ethyl-1,2,4-thiadiazol-5-ylthiomethyl)-3-cephem-4-carboxylic acid
7β-hydroxy-3-(thiazol-5-ylthiomethyl)-3-cephem-4-carboxylic acid
7β-hydroxy-3-(2-methylthiazol-5-ylthiomethyl)-3-cephem-4-carboxylic acid
7β-hydroxy-3-(4-methylthiazol-5-ylthiomethyl)-3-cephem-4-carboxylic acid
7β-hydroxy-3-(2,4-dimethylthiazol-5-ylthiomethyl)-3-cephem-4-carboxylic acid
7β-hydroxy-3-(2-ethylthiazol-5-ylthiomethyl)-3-cephem-4-carboxylic acid
7β-hydroxy-3-(4-ethylthiazol-5-ylthiomethyl)-3-cephem-4-carboxylic acid
7β-hydroxy-3-(2,4-diethylthiazol-5-ylthiomethyl)-3-cephem-4-carboxylic acid
7β-hydroxy-3-(1,3,4-oxadiazol-2-ylthiomethyl)-3-cephem-4-carboxylic acid
7β-hydroxy-3-(5-methyl-1,3,4-oxadiazol-2-ylthiomethyl)-3-cephem-4-carboxylic acid
7β-hydroxy-3-(oxazol-5-ylthiomethyl)-3-cephem-4-carboxylic acid
7β-hydroxy-3-(2-methyloxazol-5-ylthiomethyl)-3-cephem-4-carboxylic acid
7β-hydroxy-3-(4-methyloxazol-5-ylthiomethyl)-3-cephem-4-carboxylic acid
7β-hydroxy-3-(2,4-dimethyloxazol-5-ylthiomethyl)-3-cephem-4-carboxylic acid
7β-hydroxy-3-(2-ethyloxazol-5-ylthiomethyl)-3-cephem-4-carboxylic acid
7β-hydroxy-3-(4-ethyloxazol-5-ylthiomethyl)-3-cephem-4-carboxylic acid
7β-hydroxy-3-(2,4-diethyloxazol-5-ylthiomethyl)-3-cephem-4-carboxylic acid
7β-hydroxy-3-(tetrazol-5-ylthiomethyl)-3-cephem-4-carboxylic acid
7β-hydroxy-3-(1-ethyltetrazol-5-ylthiomethyl)-3-cephem-4-carboxylic acid
7β-hydroxy-3-(1,2,4-triazol-3-ylthiomethyl)-3-cephem-4-carboxylic acid
7β-hydroxy-3-(5-methyl-1,2,4-triazol-3-ylthiomethyl)-3-cephem-4-carboxylic acid
7β-hydroxy-3-(1-methyl-1,2,4-triazol-5-ylthiomethyl)-3-cephem-4-carboxylic acid
7β-hydroxy-3-(1,5-dimethyl-1,2,4-triazol-3-ylthiomethyl)-3-cephem-4-carboxylic acid
7β-hydroxy-3-(4,5-dimethyl-1,2,4-triazol-3-ylthiomethyl)-3-cephem-4-carboxylic acid
7β-hydroxy-3-(4-ethyl-1,2,4-triazol-3-ylthiomethyl)-3-cephem-4-carboxylic acid
7β-hydroxy-3-(5-ethyl-1,2,4-triazol-3-ylthiomethyl)-3-cephem-4-carboxylic acid 7β-hydroxy-3-(1-ethyl-1,2,4-triazol-5-ylthiomethyl)-3-cephem-4-carboxylic acid 7β-hydroxy-3-(4,5-diethyl-1,2,4-triazol-3-ylthiomethyl)-3-cephem-4-carboxylic acid 7β-hydroxy-3-(1,3-diethyl-1,2,4-triazol-5-ylthiomethyl)-3-cephem-4-carboxylic acid 7β-hydroxy-3-(4-methoxymethyl-1,2,4-triazol-3-ylthiomethyl)-3-cephem-4-carboxylic acid 7β-hydroxy-3-(4-methyl-5-trifluoromethyl-1,2,4-triazol-3-ylthiomethyl)-3-cephem-4-carboxylic acid 7β-hydroxy-3-(1,2,3-triazol-4-ylthiomethyl)-3-cephem-4-carboxylic acid 7β-hydroxy-3-(3-methyl-1,2,3-triazol-4-ylthiomethyl)-3-cephem-4-carboxylic acid 7β-hydroxy-3-(5-methyl-1,2,3-triazol-4-ylthiomethyl)-3-cephem-4-carboxylic acid 7β-hydroxy-3-(3,5-dimethyl-1,2,3-triazol-4-ylthiomethyl)-3-cephem-4-carboxylic acid 7β-hydroxy-3-(3-ethyl-1,2,3-triazol-4-ylthiomethyl)-3-cephem-4-carboxylic acid 7β-hydroxy-3-(5-ethyl-1,2,3-triazol-4-ylthiomethyl)-3-cephem-4-carboxylic acid 7β-hydroxy-3-(3,5-diethyl-1,2,3-triazol-4-ylthiomethyl)-3-cephem-4-carboxylic acid 7β-hydroxy-3-(3-methoxymethyl-1,2,3-triazol-4-ylthiomethyl)-3-cephem-4-carboxylic acid 7β-hydroxy-3-(4-pyridylthiomethyl)-3-cephem-4-carboxylic acid 7β-hydroxy-3-(3-pyridylthiomethyl)-3-cephem-4-carboxylic acid 7β-hydroxy-3-(4-pyrimidylthiomethyl)-3-cephem-4-carboxylic acid 7β-hydroxy-3-(2-pyrazinylthiomethyl)-3-cephem-4-carboxylic acid.

EXAMPLE 8

When a 7β-hydroxy-3-heterocyclicthiomethyl-3-cephem-4-carboxylic acid t-butyl ester prepared in Example 7 is esterified with an esterifying agent known to the art, particularly with an acid or activated form of an acid listed below, suitably protected as necessary:

α-hydroxyphenylacetic acid
α-aminophenylacetic acid
α-amino-4-hydroxyphenylacetic acid
trifluoromethylmercaptoacetic acid
methylmercaptoacetic acid
2,2,2-trifluoroethylsulfinylacetic acid
2-thienylacetic acid
1-tetrazolylacetic acid
phenoxyacetic acid
α-carboxy-2-thienylacetic acid
α-carboxyphenylacetic acid
α-sulfophenylacetic acid
methylsulfonylacetic acid
cyanomethylmercaptoacetic acid
α-amino-4-carboxymethylaminophenylacetic acid
α-amino-3-fluoro-4-hydroxyphenylacetic acid
3-sydnoneacetic acid
4-pyridylthioacetic acid
2-aminomethylphenylacetic acid according to the procedures of Examples 2, 3, 4 or 5 with removal of the protective groups where appropriate as described therein, the corresponding 7β-acyloxy-3-heterocyclicthiomethyl-3-cephem-4-carboxylic acids are prepared.

EXAMPLE 9

The sodium salt of 7β-trifluoromethylmercaptoacetoxycephalosporanic acid is prepared by dissolving the acid in ethyl acetate, adding a sodium 2-ethylhexanoate solution and then slowly adding ether until the sodium salt is precipitated.

Sodium salts of the other cephalosporins disclosed above may be similarly prepared.

The sodium salt of 7β-trifluoromethylmercaptoacetoxycephalosporanic acid is converted to the free acid by treating an aqueous solution of the salt with Amberlite IR-120H ion exchange resin.

EXAMPLE 10

An injectable pharmaceutical composition is prepared by dissolving 100–150 mg. of 7β-trifluoromethylmercaptoacetoxycephalosporanic acid sodium salt in sterile water or sterile normal saline solution (1–2 ml.)

All other cephalosporin compounds within this invention are formulated in a similar manner.

I claim:

1. A compound of the formula:

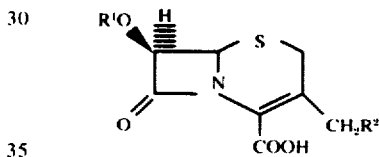

in which:

$R^1$ is

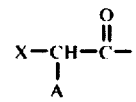

where:

X is thienyl; dihydrophenyl; phenyl; phenyl monosubstituted with hydroxy, hydroxymethyl, formamido, ureido, carboxymethylamino; 3-fluoro-4-hydroxyphenyl or 3,4-dihydroxyphenyl;

A is $NH_2$, OH, COOH or $SO_3H$; or formyloxy when X is phenyl; and $R^2$ is acetoxy, or a non-toxic pharmaceutically acceptable salt thereof.

2. A compound according to claim 1, said compound being 7β-(α-aminophenylacetoxy)cephalosporanic acid.

3. A compound according to claim 1, said compound being 7β-(α-hydroxyphenylacetoxy)cephalosporanic acid.

* * * * *